United States Patent [19]

Greiner et al.

[11] Patent Number: 5,124,344
[45] Date of Patent: Jun. 23, 1992

[54] COMPOUNDS CONTAINING TRIAZOLE GROUPS AND USE THEREOF AS FUNGICIDES

[75] Inventors: Alfred Greiner, St-Cyr-au-Mt-d'Or; Régis Pepin, Rilleux-la-Pape, both of France

[73] Assignee: Rhone-Poulenc Agrochimie, Lyons, France

[21] Appl. No.: 265,520

[22] Filed: Nov. 1, 1988

Related U.S. Application Data

[63] Continuation-in-part of Ser. No. 889,313, Jul. 23, 1986, Pat. No. 4,863,943, which is a continuation-in-part of Ser. No. 693,281, Jan. 22, 1985, abandoned.

[30] Foreign Application Priority Data

Oct. 29, 1987 [FR] France ............... 87 15246

[51] Int. Cl.⁵ ................ A01N 43/653; C07D 249/08
[52] U.S. Cl. ................ 514/383; 548/267.8; 548/268.2; 548/268.6
[58] Field of Search .......... 548/262, 267.8, 268.6; 514/383

[56] References Cited

U.S. PATENT DOCUMENTS 4,863,943 9/1989 DeBourge et al. ............ 548/262

Primary Examiner—Patricia L. Morris
Attorney, Agent, or Firm—Scully, Scott, Murphy & Presser

[57] ABSTRACT

The invention relates to compounds of formula:

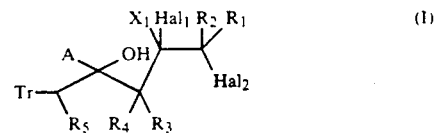

A is the group $(Y)_n Ph-(CH_2)_m$ where Ph is a phenyl nucleus and $m=0$ or 1, preferably 0,
Y is a halogen atom or a cyano or nitro group or an optionally halogenated alkyl or alkoxy group,
n is a positive integer or zero, smaller than 6,
Tr denotes a 1,2,4-triazol-1-yl group,
$R_1$ to $R_5$ denote the hydrogen atom or a lower alkyl radical,
$X_1$ denotes a hydrogen atom or a hydrocarbyl radical.
Hal1 and Hal2, which are identical or different, denote a halogen atom, preferably chosen from chlorine or bromine and advantageously Hal1 and hal2 are identical.

Use of these compounds as fungicides.

17 Claims, No Drawings

COMPOUNDS CONTAINING TRIAZOLE GROUPS AND USE THEREOF AS FUNGICIDES

This is a continuation-in-part of U.S. patent application Ser. No. 889,313, filed Jul. 23, 1986, now U.S. Pat. No. 4,863,943, issued on Sep. 5, 1989, which is a continuation-in-part of U.S. patent application Ser. No. 693,281, filed Jan. 22, 1985, now abandoned.

The present invention relates to new compounds containing triazole or imidazole groups for use in plant protection. It also relates to the processes for preparing the said compounds. It further relates to the use of these compounds as fungicides, to the fungicidal compositions based on these compounds and to the processes for combating fungal diseases of crops by using these compounds.

Many compounds containing triazole groups, particularly fungicides, are already known, in particular from European Patent Application EP-A-0,047,594.

An objective of the present invention is to provide compounds exhibiting improved properties in the treatment of fungal diseases. In particular, these compounds exhibit improved properties in the treatment of piriculariose, of mildews and of rusts, especially of cereals.

They are characterized in that they correspond to the formula I, shown at the end of the description, in which:

A is the group $(Y)_n Ph-(CH_2)_m$ where Ph is a phenyl nucleus and m=0 or 1, preferably 0.

Y is a halogen atom or a cyano or nitro group, or an alkyl or alkoxy, phenyl, phenoxy, benzyl or benzyloxy group, these groups being halogenated if desired.

n is an integer, positive or zero, lower than 6, it being possible for the groups Y to be identical or different when n is greater than 1, Tr denotes a 1,2,4-triazol-1-yl group. Im denotes a 1,3-imidazol-1-yl group $R_1$ to $R_5$, which are identical or different, denote the hydrogen atom or a lower alkyl, lower cycloalkyl, aryl (especially phenyl), aralkyl (especially benzyl), lower alkoxy, lower alkanoyl or aroyl (especially benzoyl) radical, it being possible for these various radicals to be substituted, if desired (for example by one or more atoms or radicals such as halogen atoms and lower alkoxy radicals).

$X_1$ denotes the hydrogen atom, a halogen atom, a lower alkyl radical, a lower cycloalkyl radical, an aryl (especially phenyl) or aralkyl (especially benzyl) radical, it being possible for these various radicals to be substituted, if desired, similarly to groups $R_1$ to $R_5$, a group $Q-R_6$ in which Q denotes O or S, and $R_6$ denotes the hydrogen atom or a lower alkyl radical, a lower cycloalkyl, aryl (especially phenyl) aralkyl (especially benzyl), acyl or thioacyl (especially acetyl, thioacetyl, propionyl, thiopropionyl), alkyloxythioyl, aryloxythioyl or aralkyloxythioyl radical (the term thioyl corresponds to C=S(S)), it being possible for these radicals to be substituted similarly to groups $R_1$ to $R_5$, a group $-NR_8R_9$, in which $R_8$ and $R_9$, which are identical or different, denote the hydrogen atom or a lower alkyl radical, a lower cycloalkyl, aryl (especially phenyl) or aralkyl (especially benzyl) radical, it being possible for these various radicals to be substituted, if desired, similarly to groups $R_1$ to $R_5$, or else $R_8$ and $R_9$ may together form a single divalent hydrocarbon radical containing from 3 to 6 carbon atoms, it being possible for one of these carbon atoms to be replaced by an oxygen, sulphur or nitrogen atom, the said single divalent radical being itself substituted, if desired (for example by one or more halogen atoms or optionally halogenated lower alkyl, or lower alkoxy radicals or hydroxy). Hal1, Hal2, which are identical or different, denote a halogen atom, preferably chosen from chlorine or bromine and advantageously Hal1 and Hal2 are identical.

The invention also relates to the salt forms of the compounds according to the invention. The salt forms are the agriculturally acceptable forms, among which there may be mentioned: the hydrochloride, sulphate, oxalate, nitrate or arylsulphonate, as well as the addition complexes of these compounds with metal salts and especially with iron, chromium, copper, manganese, zinc, cobalt, tin, magnesium and aluminium salts.

By way of example, complexes with zinc may be obtained by reacting the compound of formula I with zinc chloride.

Within the meaning of the present text, it is understood that the adjective "lower", when qualifying an organic radical, means that this radical contains at most six carbon atoms. This radical may be linear or branched.

The Applicant wishes to emphasize that the appended plates should not be considered as being drawings in any way whatsoever, but as forming an integral part of the description for the invention.

The compounds of the formula I and the compounds which, if desired, can be employed as intermediates in the preparative processes, and which will be defined on the occasion when these processes are described can exist in one or more isomeric forms, according to the number of asymmetric centres in the molecule. The invention therefore relates both to all the optical isomers and to their racemic mixtures and the corresponding diastereoisomers. The separation of the diastereoisomers and/or of the optical isomers may be carried out according to methods which are known per se.

In view of the fungicidal applications it has been found that the invention preferably related to the compounds of formula I in which Y is a halogen and n=1, 2 or 3.

It has also been found that it was preferable to employ the compounds of formula I in which n=1 or 2, and Y is a halogen atom placed in an ortho and/or para position.

Also preferably, n=2 and Y is a halogen atom, advantageously chlorine placed in an ortho and in the para position.

The preferred compounds of the formula I are those in which the groups $R_1$ to $R_5$ and $X_1$ correspond to a hydrogen atom or to a lower alkyl group and/or Hal1 and Hal2 both correspond to the chlorine atom.

Also preferably, the groups $R_1$ to $R_5$ and $X_1$ correspond to a hydrogen atom.

The compound containing a triazole group is to be preferred.

The present invention also relates to the processes for preparing the compounds according to the invention.

Step a

A haloketone of formula IIa, obtained by a known process, in which A and $R_5$ have the same meaning as that given in the case of the compounds of formula I, and Z corresponds to a halogen atom, is reacted with an organometallic compound of formula IIb, in which $R_1$ to $R_4$ and $X_1$ have the same meaning as above and M corresponds to an alkali metal or to a magnesium compound (MgHal) or to a zinc compound (ZnHal), for example, in a solvent preferably chosen from ethers such as diethyl ether or tetrahydrofuran, aliphatic, alicyclic or aromatic hydrocarbons such as hexane or toluene, at a temperature chosen between $-50°$ C. and the reflux of the solvent in question and in a molar ratio IIa:IIb of preferably between 1.1 and 0.2. The reaction results in the compound of formula IIc after neutralization of the reaction mixture. This process is described in EP-A-0,033,501.

Step b

The compound of formula IIc is subsequently reacted with an unsubstituted triazole or imidazole in the presence of organic or inorganic base, for example pyridine, triethylamine, sodium hydroxide, potassium hydroxide, alkali metal or alkaline-earth metal carbonates and bicarbonates, and in a suitable solvent such as, for example, alcohols, ketones, amides, nitriles and aromatic hydrocarbons, halogenated if desired, at a temperature between $80°$ and the reflux of the solvent and in a molar ratio IIOc: imidazole or triazole preferably between 1.1 and 0.2, and this results in the compound of formula IId. The reaction generally takes place via an epoxide intermediate of formula IIe which may, if desired, be isolated or prepared separately by methods which are known to the person skilled in the art. For example, by reacting the compound IIc with one of the abovementioned bases. See, for example, the process described in EP-A-0,097,425.

In all cases, the grafting step is advantageously performed in the presence of an acid-acceptor, in an anhydrous or nonanhydrous medium, in a solvent which is inert under the reaction conditions, generally between $50°$ and $180°$ C. and preferably at a temperature close to the boiling point of the solvent. As acid-acceptors there may be mentioned inorganic bases such as, for example, sodium hydroxide or potassium hydroxide, alkali metal or alkaline-earth metal carbonates, nitrogenous bases such as triethylamine, quaternary amines such as tetrabutylammonium hydroxide, or phosphonium hydroxides. The solvents employed may be advantageously polar aprotic solvents such as, for example, dimethylformamide, dimethylacetamide, dimethyl sulphoxide, acetone, methyl ethyl ketone, acetonitrile, N-methylpyrrolidone, or polar protic solvents such as methanol or propanol. If desired, this reaction may be carried out in the presence of a suitable catalyst. As a catalyst which may be employed, phase-transfer catalysts may be mentioned, such as, for example, quaternary ammonium derivatives like tetrabutylammonium chloride.

The reaction is preferably carried out in a molar excess of triazole or imidazole derivative which is preferably between 1.05 and 1.5.

When a solvent is employed, it will be preferred to work in a dilute medium containing 1% to 70% by weight of compound of formula IIc, IIe relative to the total solution.

The acid-acceptor is present in at least a stoichiometric quantity as an equivalent of the labile hydrogen atom of the triazole or imidazole. In general, a molar equivalent ratio between 1 and 2.5 will be satisfactory.

It is obvious that the salt derivative of the triazole or imidazole may be prepared separately and, in this case, the presence of an acid-acceptor is not needed for the grafting reaction. This preparation is carried out in an anhydrous or nonanhydrous medium in a solvent under the same operating conditions as those described in the case of the in situ formation of the triazole or imidazole derivative converted into a salt.

Step c

One molecule of halogen or of mixed halogen is added to the compound IId, preferably mole per mole, in an inert solvent such as optionally halogenated aromatic or saturated hydrocarbons, and this results in the compound I. This addition may also be carried out in a concentrated inorganic acid medium, which has the advantage of causing the compound I to precipitate in the form of the corresponding salt.

The present invention also relates to the use of the compounds of the formula I as fungicides.

The compounds according to the invention may be employed for both preventive and curative combat against fungi, especially of the basidiomycetes, ascomycetes, adelomycetes or fungi-imperfecti type, in particular rusts, mildew, root-rot, fusarioses, helminthosporioses, septorioses and rhizoctones of vegetables and of plants in general and in particular of cereals such as wheat, barley, rye, oats, and their hybrids and also rice and corn. The compounds according to the invention are active in particular against fungi especially of the basidiomycetes, ascomycetes, adelomycetes or fungi-imperfecti type such as *Botrytis cinerea, Erysiphe graminis, Puccinia recondita, Piricularia oryzae, Cercospora beticola, Puccinia striiformis, Erysiphe cichoracearum, Fusarium oxysporum* (melonis), *Pyrenophora avenae, Septoria nodorum, Septoria tritici, Venturia inaequalis, Whetzelinia sclerotiorum, Monilia laxa, Mycosphaerella fijiensis, Marssonina panattoniana, Alternaria solani, Aspergillus niger, Cercospora arachidicola, Cladosporium herbarum, Helminthosporium oryzae, Penicillium expansum, Pestalozzia sp., Phialophora cinerescens, Phoma betae, Phoma foveata, Phoma lingam, Ustilago maydis, Verticillium dahliae, Ascochyta pisi, Guignardia bidwellii, Corticium rolfsii, Phomopsis viticola, Sclerotinia sclerotiorum, Sclerotinia minor, Coryneum cardinale* and *Rhizoctonia solani.*

They are also and still active against the following fungi: *Acrostalagmus koningi*, the Alternaria, the Colletotrichum, *Corticium rolfsii, Diplodia natalensis, Gaeumannomyces graminis, Gibberella fujikuroi, Hormodendron cladosporioides, Lentinus degener* or *tigrinus, Lenzites quercina, Memnoniella echinata, Myrothecium verrucaria, Paecylomyces varioti, Pellicularia sasakii, Phellinus megaloporus, Polystictus sanguineus, Poria vaporaria, Sclerotium rolfsii, Stachybotris atra*, the Stereum, Stilbum sp. *Trametes trabea, Trichoderma pseudokoningi* and *Trichothecium roseum.*

The compounds of the invention are especially advantageous because of their wide spectrum in respect of the diseases of the cereals (mildew, rust) and of rice (piriculariosis). They may also be of great interest because of their activity on gray rot (Botrytis) and on cercosporioses, and, as a result, they may be applied to crops as varied as vine, market garden crops and arboriculture and tropical crops such as the peanut, banana, coffee tree, pecan nut and others.

The compounds may also be employed in the treatment of seeds (cereals, cotton plant, beet, rape, fodder grains), for example in the form of coating or film-coating. Thus, a form of application can be found in U.S. Pat. No. 3,989,501, col 7, l 17-23. Similarly, in FR-A-2,588,442. It will also be possible to employ aqueous streams.

In general, these formulations are already known; see, for example "Catalogue of pesticide formulation types and international coding system" published by the GIFAP technical monograph No. 2, pages 12 to 14, revised in January 1984.

Besides the applications already described above, the products according to the invention also exhibit an excellent biocidal activity towards many other varieties of microorganisms, among which there may be mentioned, without any limitation being implied, fungi such as those of the genera:

Pullularia such as the species *P. pullulans*,
Chaetomium such as the species *C. globosum*,
Aspergillus such as the species *Aspergillus niger*,
Coniophora such as the species *C. puteana*.

Because of their biocidal activity, the products of the invention make it possible to combat effectively the microorganisms whose proliferation gives rise to many problems in the argricultural and industrial fields. To this end, they are most especially suitable for the protection of plants or of industrial products such as wood, leather, paints, paper, ropework, plastics and industrial water circuits.

They are very particularly suited to the protection of lignocellulosic products and especially of wood, be it furniture or structural timber or timber exposed to inclement weather such as fencing timber, vine stakes or railway sleepers.

The compounds according to the invention, employed by themselves or in the form of compositions such as defined hereinafter in wood treatments, are generally used with organic solvents and may be associated, if desired, with one or more known biocidal products such as pentachlorophenol, metal salts, especially those of copper, manganese, cobalt, chromium and zinc, derived from inorganic or carboxylic acids (heptanoic, octanoic, naphthenic acids), organic tin complexes, mercaptobenzothiazole, and insecticides such as the pyrethroids or organic chlorine derivatives.

Finally, they exhibit an excellent selectivity for crops.

They are applied advantageously in dosages of 0.005 to 5 kg/ha, and more specifically of 0.01 to 0.5 kg/ha.

For their use in practice, the compounds according to the invention are rarely employed by themselves. In most cases they form part of compositions. These compositions, which may be employed to protect plants against fungal diseases, or in compositions for controlling plant growth, contain, as active substance, a compound according to the invention such as described above in combination with agriculturally acceptable solid or liquid carriers and/or surface-active agents, also agriculturally acceptable. In particular, the usual inert carriers and the usual surface-active agents can be employed.

The term "carrier", in the present description, denotes a natural or synthetic, organic or inorganic substance with which the active substance is associated to facilitate its application to the plant, to the seeds or to the soil. This carrier is therefore generally inert and it must be agriculturally acceptable, especially on the treated plant. The carrier may be solid (clays, natural or synthetic silicates, silica, resins, waxes, solid fertilizers, and the like) or liquid (water, alcohols, ketones, oil fractions, aromatic or paraffinic hydrocarbons, chlorinated hydrocarbons, liquefied gases, and the like).

The surface-active agent may be an emulsifying, dispersing or wetting agent of ionic or nonionic type. There may be mentioned, for example, salts of polyacrylic acids, salts of lignosulphonic acids, salts of phenolsulphonic or naphthalenesulphonic acids, polycondensates of ethylene oxide with fatty alcohols or with fatty acids or with fatty amines, substituted phenols (especially alkylphenols or arylphenols), salts of esters of sulphosuccinic acids, taurine derivatives (especially alkyltaurates), and phosphoric esters of alcohols or of phenols polycondensed with ethylene oxide. The presence of at least one surface-active agent is generally indispensable when the active substance and/or the inert carrier are not soluble in water and when the vector agent in the application is water.

For their application, the compounds of the formula (I) are therefore generally to be found in the form of compositions; these compositions according to the invention are themselves in quite diverse, solid or liquid forms.

As solid forms of compositions there may be mentioned powders for dusting or spraying (with a content of compound of formula (I) which may go up to 100%) and granulates, especially those obtained by extrusion, by compacting, by impregnation of a granular carrier, or by granulation from a powder (the content of compound of formula (I) in the these granulates being between 1 and 80% in these latter cases).

As forms of compositions which are liquid or intended to constitute liquid compositions during the application, there may be mentioned solutions, especially water-soluble concentrates, emulsifiable concentrates, emulsions, flowables, aerosols, wettable powders (or spraying powder) and pastes.

The emulsifiable or soluble concentrates in most cases contain 10 to 80% of active substance, while ready for use emulsions or solutions contain, in their case, 0.01 to 20% of active substance.

These compositions may also contain all kinds of other ingredients such as, for example, protective colloids, adhesives, thickeners, thixotropic agents, penetrating agents, stabilizers, sequestrants, and the like, as well as other known active substances with pesticidal properties (especially insecticides or fungicides) or with properties which promote plant growth (especially fertilizers) or with properties controlling plant growth. More generally, the compounds according to the invention may be combined with any solid or liquid additives corresponding to the usual formulation techniques.

For example, in addition to the solvent, the emulsifiable concentrates may, when necessary, contain 2 to 20% of suitable additives such as stabilizers, surface-active agents, penetrating agents, corrosion inhibitors, colorants or adhesives, referred to above.

In the case of a use of the compounds according to the invention as fungicides, the use dosages may vary within wide limits, especially depending on the virulence of the fungi and the climatic conditions.

As a general rule, compositions containing 0.5 to 5,000 ppm of active substance are suitable; these values are indicated for the compositions which are ready for application. Ppm means "parts per million". The range from 0.5 to 5,000 ppm corresponds to a range from $5 \times 10^{-5}$ to 0.5% (percentages by weight).

Insofar as the compositions which are adapted to storage and to transport are concerned, these more advantageously contain from 0.5 to 95% (by weight) of active substance.

Thus, therefore, the compositions for agricultural use according to the invention may contain the active substances according to the invention in very wide limits, ranging from $5 \times 10^{-5}\%$ to 95% (by weight).

By way of example, here is the composition of a few concentrates:

| Example F (formulation) 1 | |
|---|---|
| active substance | 400 g/l |
| alkali metal dodecylbenzenesulphonate | 24 g/l |
| nonylphenol condensate with 10 molecules of ethylene oxide | 16 g/l |
| cylohexanone | 200 g/l |
| aromatic solvent | q.s. 1 liter |

According to another formula of an emulsifiable concentrate, the following are employed:

| Example F 2 | |
|---|---|
| active substance | 250 g |
| epoxidized vegetable oil | 25 g |
| mixture of alkylarylsulphonate and of polyglycol ether and of fatty alcohols | 100 g |
| dimethylformamide | 50 g |
| xylene | 575 g |

Emulsions of any desired concentration, which are particularly suitable for application to foliage can be obtained from these concentrates by diluting with water.

Flowables, also applicable in spraying, are prepared so as to obtain a stable fluid product which does not settle and they usually contain from 10 to 75% of active substance, from 0.5 to 15% of surface-active agents, from 0.1 to 10% of thixotropic agents, from 0 to 10% of suitable additives such as antifoams, corrosion inhibitors, stabilizers, penetrating agents and adhesives and, as a carrier, water or an organic liquid in which the active substance is poorly soluble or insoluble; certain organic solid substances or inorganic salts may be dissolved in the carrier to help to prevent sedimentation, or as antifreezes in the case of water.

Wettable powders (or spraying powder) are usually prepared so that they contain 5 to 95% of active substance and, in addition to the solid carrier, they usually contain from 0 to 5% of a wetting agent, from 3 to 10% of a dispersing agent and, when needed, from 0 to 10% of one or more stabilizers and/or other additives such as penetrating agents, adhesives or anticaking agents, colorants, and the like.

By way of example, here are various compositions of wettable powders:

| Example F 3 | |
|---|---|
| active substance | 50% |
| calcium lignosulphonate (deflocculant) | 5% |
| isopropylnaphthalenesulphonate (anionic wetting agent) | 1% |
| anticaking silica | 5% |
| kaolin (filler) | 39% |

Another composition of a 70% strength spraying powder employs the following constituents:

| Example F 4 | |
|---|---|
| active substance | 700 g |
| sodium dibutylnaphthylsulphonate | 50 g |
| product of condensation, in proportions of 3/2/1, of naphthalenesulphonic acid, of | 30 g |

| -continued | |
|---|---|
| Example F 4 | |
| phenolsulphonic acid and of formaldehyde | |
| kaolin | 100 g |
| Champagne chalk | 120 g |

Another composition of 40% strength spraying powder employs the following constituents:

| Example 5: | |
|---|---|
| active substance | 400 g |
| sodium lignosulphonate | 50 g |
| sodium dibutylnaphthalenesulphonate | 10 g |
| silica | 540 g |

Another composition of 25% strength spraying powder employs the following constituents:

| Example F 6: | |
|---|---|
| active substance | 250 g |
| calcium lignosulphonate | 45 g |
| mixture of equal weights of Champagne chalk and of hydroxyethyl cellulose | 19 g |
| sodium dibutylnaphthalenesulphonate | 15 g |
| silica | 195 g |
| Champagne chalk | 195 g |
| kaolin | 281 g |

Another compositon of 25% strength spraying powder employs the following constituents:

| Example F 7: | |
|---|---|
| active substance | 250 g |
| isooctylphenoxy-polyoxyethylene-ethanol | 25 g |
| mixture of equal weights of Champagne chalk and of hydroxyethyl cellulose | 17 g |
| sodium aluminosilicate | 543 g |
| kieselguhr | 165 g |

Another composition of 10% strength spraying powder employs the following constituents:

| Example F 8: | |
|---|---|
| active substance | 100 g |
| mixture of sodium salts of saturated fatty acid sulphates | 30 g |
| product of condensation of naphthalenesulphonic acid with formaldehyde | 50 g |
| kaolin | 820 g |

To obtain these spraying powders or wettable powders, the active substances are mixed thoroughly with the additional substances in suitable mixers and are ground with the aid of mills or other suitable grinders. Spraying powders whose wettability and dispersion are advantageous are thereby obtained; they can be suspended in water at any desired concentration and these suspensions can be very advantageously employed, in particular for application to plant foliage or seeds.

Pastes can be produced instead of wettable powders. The conditions and methods of producing and of using these pastes are similar to those for wettable powders or spraying powders.

As has already been stated, aqueous dispersions and emulsions, for example the compositions obtained by diluting a wettable powder or an emulsifiable concentrate according to the invention with water, are included within the general scope of the present invention. The emulsions may be the water-in-oil or oil-in-water type and they may have a thick consistency like that of a mayonnaise.

The granulates intended to be dropped onto the soil are usually prepared so that they are between 0.1 and 2 mm in size and they can be manufactured by agglomeration or impregnation. In general, the granulates contain 0.5 to 25% of active substance and 0 to 10% of additives such as stabilizers, slow-release modifying agents, binders and solvents.

According to an example of granulate composition, the following constituents are employed:

| Example F |  |
|---|---|
| active substance | 50 g |
| epichlorohydrin | 2.5 g |
| cetyl polyglycol ether | 2.5 g |
| polyethylene glycol | 35 g |
| kaolin (particle size 0.3 to 0.8 mm) | 910 g |

In this particular case, the active substance is mixed with epichlorohydrin and 60 g acetone are used to form a solution; polyethylene glycol and cetyl polyglycol ether are then added. Kaolin is watered with the solution obtained and acetone is then evaporated off under vacuum. A microgranulate of this kind is advantageously employed for combating soil fungi.

The compounds of formula (I) may also be employed in the form of dusting powders; thus, a composition comprising 50 g of active substance and 950 g of talc may be employed; it is also possible to employ a composition comprising 20 g of active substance, 10 g of finely divided silica and 970 g of talc; these constituents are mixed and ground and the mixture is applied by dusting.

Examples I to VII illustrate individual methods of preparing compounds according to the invention and these compounds themselves. The nomenclature of the compounds (in the original French text) has been given according to French standards except that numbering of the substituents precedes the substituents themselves.

EXAMPLE I

Preparation of
1-[2-(2,4-dichlorophenyl)-2-hydroxy-4,5-dibromopentyl](1H)1,2,4-triazole

Step a

Preparation of
1-chloro-2-(2,4-dichlorophenyl)-4-penten-2-ol

An organomagnesium derivative is prepared by adding a solution of allyl bromide (180 ml) in tetrahydrofuran (400 ml) to a suspension of magnesium (126 g) in tetrahydrofuran (400 ml) at 10° C.

A solution of alpha-trichloro-2,4-acetophenone (232 g) in tetrahydrofuran (250 ml) is added at −10° C., and the mixture is neutralized with acetic acid. It is washed with water, dried and evaporated down. A colourless oil (258 g) is obtained. Boiling point $(3 \times 10^{-2}$ mm Hg)$=140°$–$142°$ C.

Step b

Preparation of
1-[2-(2,4-dichlorophenyl)-2-hydroxy-4-pentenyl](1H)1,2,4-triazole A mixture of the product obtained in step a) (106 g), of triazole (55 g) and of potassium carbonate (160 g) is heated for four hours at 120° in dimethylformamide (600 ml). The insoluble materials are filtered off, are washed with dimethylformamide and the reaction mixture is concentrated under vacuum. The residue, dissolved in methylene chloride, is washed with water and then concentrated. The product is obtained by crystallization from ethyl acetate after dilution with heptane. A pale pink solid (97 g), melting at 101°, is isolated.

Step c

Preparation of compound No. 1

The compound obtained in step b (35 g) in chloroform (200 ml) is treated with bromine at 0°. After the disappearance of colour, the solvent is evaporated off. A solid which has a melting point of 116° C. is obtained.

EXAMPLE II

Preparation of
1-[2-(2,4-dichlorophenyl)-2-hydroxy-4,5-dichloropentyl](1H)1,2,4-triazole. Compound No. 2

The chlorohydrin (113 g) obtained in step a of Example I, dissolved in DMF (100 ml) is run into a mixture of $K_2CO_3$ (207 g) and of 1,2,4-triazole (35.9 g) in DMF (900 ml) at 125° C. After heating at 125° C., filtration of the insolubles and evaporation, washing and recrystallization, the triazole derivative IId (103 g) is obtained in the form of a light-brown solid.

This triazole derivative, dissolved in concentrated aqueous HCl, is treated with chlorine until the yellow colour persists. The mixture is then left at ambient temperature and is then diluted. The precipitate formed is filtered off and treated with aqueous sodium bicarbonate. After extraction, drying, evaporation and crystallization, a white solid is obtained. Melting point 126° C.

The following compounds are obtained in the same manner:

1-[2-(4-Chlorophenyl)-2-hydroxy-4,5-dichloropentyl](1H)1,2,4-triazole Compound No. 3 M.p. 82° C.
1-[2-(2,4-Dichlorophenyl)-2-hydroxy-3-methyl-4,5-dibromopentyl](1H)1,2,4-triazole. Compound No. 4. Oil.
1-[2-(2,4-Dichlorophenyl)-2-hydroxy-3-methyl-4,5-dichloropentyl](1H)1,2,4-triazole. Compound No. 5. Oil.

Examples III to V illustrate the fungicidal applications of the compounds according to the invention.

In these examples, the spraying operations with solutions or suspensions of active substances are carried out under such conditions that the spraying of a solution or suspension at a concentration equal to 1 g/l corresponds on average to the application of approximately 2 micrograms of active substance per cm² of plant foliage.

An aqueous emulsion of the active substance to be tested, having the following composition, is prepared by fine grinding:

active substance to be tested: 60 mg
Tween 80 (surface-active agent) consisting of an oleate of an ethylene oxide polycondensate derivative of sorbitan) diluted to 10% strength in water: 0.3 ml made up to 60 ml with water.

This aqueous emulsion is then diluted with water to obtain the desired concentration.

In these examples it is considered that a product provides a total protection against a fungal disease when the protection is at least 95%.

EXAMPLE III

In vivo test on Piricularia oryzae, responsible for the piriculariosis of rice (rice blast)

Rice, in cups, sown in a 50/50 mixture of enriched peat and pozzolana, is treated at the stage when it is 10 cm in height by spraying with an aqueous emulsion (called spraying mixture) as defined above. The test is repeated twice. After 24 hours it is inoculated by the application to the foliage of a suspension of spores obtained as a pure culture (500 spores/ml).

The contaminated plants are placed in an incubation cell at 25° C. and 100% relative humidity for 24 h before being placed in an observation cell.

The reading is taken 8 days after the contamination. Under these conditions, a total protection is observed at 1 g/l in the case of the compounds 1, 2, 3, 4 and 5.

EXAMPLE IV

In vivo test on *Erysiphe graminis* on barley (barley mildew)

Barley, in cups, sown in a 50/50 mixture of enriched peat and pozzolana is treated at the stage when it is 10 cm in height by spraying with an aqueous emulsion (called spraying mixture) at the concentration indicated above. The test is repeated twice. After 24 hours the barley plants are dusted with spores of *Erysiphe graminis*, the dusting being carried out with the aid of diseased plants.

The reading is taken 8 to 14 days after the contamination.

Under these conditions, the following results are obtained: at the dosage of 1 g/l, complete protection with the compounds 1, 2, 3, 4 and 5.

EXAMPLE V

In vivo test on *Puccina recondita*, responsible for wheat rust

Wheat, in cups, sown in a 50/50 mixture of enriched peat and pozzolana, is treated at the stage when it is 10 cm in height by spraying with aqueous emulsions (called spraying mixture) as described above.

The test is repeated twice.

After 24 hours, an aqueous suspension of spores (50,000 sp/cm$^3$) is dusted onto the wheat; this suspension has been obtained from contaminated plants. The wheat is then placed for 48 hours in an incubation cell at approximately 18° C. and at 100% relative humidity.

After these 2 days, the wheat is taken to an observation cell where the relative humidity is returned to 60%. The check on the state of the plants is made between the 11th and the 15th day after the contamination, by comparison with the untreated control.

At the dosage of 1 g/l, complete protection with the compounds 1, 2, 3, 4 and 5.

EXAMPLE 6

In vitro test on seed fungi and soil fungi

The action of the compounds according to the invention on the following fungi, responsible for the diseases of cereals and other plants is investigated:

1) *Botrytis cinerea* sensitive to carbendazim and to cyclic imides
2) *Botrytis cinerea* resistant to carbendazim and to cyclic imides
3) *Fusarium oxysporum* f.sp. melonis
4) *Rhizoctonia solani*
5) *Pseudocercosporella herpotrichoides*
6) *Septoria nodorum*
7) *Fusarium culmorum*
8) *Fusarium nivale*
9) *Fusarium roseum*
10) *Helminthosporium gramineum*
11) *Pyrenophora avenae*
12) *Helminthosporium teres*
13) *Rhizoctonia cerealis*

The numbers appearing before the names will be employed to identify the fungi in the table below.

In each test, the operating procedure is as follows: a nutrient medium consisting of potato, of glucose and of agar (PDA medium) is introduced by superfusion into a series of Petri dishes (20 ml per dish) after sterilization in the autoclave at 120° C.

While the dishes are being filled, an acetone solution of the active substance is injected into the superfusion medium, to obtain the final desired concentration.

Petri dishes similar to the preceding ones, into which similar quantities of a nutrient medium, not containing any active substance, are poured, are taken as a control.

After 24 or 48 h each dish is seeded by depositing a fragment of mycelium originating from a previous culture of the same fungus.

The dishes are stored at 22° C. for 2 to 10 days (depending on the fungus tested) and the growth of the fungus in the dishes containing the active substance to be tested is then compared with that of the same fungus in the dish employed as control.

The degree of inhibition of the growth of the fungus is thus determined in the case of each compound tested, considered at a dosage of 30 ppm.

| Compound No. | Fungi | | | | | | | | | | | | |
|---|---|---|---|---|---|---|---|---|---|---|---|---|---|
| | 1 | 2 | 3 | 4 | 5 | 6 | 7 | 8 | 9 | 10 | 11 | 12 | 13 |
| 1 | 95 | 95 | 90 | 90 | 100 | 95 | 100 | 95 | 80 | 95 | 100 | 95 | 100 |
| 2 | 90 | 95 | 50 | 80 | 100 | 100 | 0 | 80 | 0 | 95 | 100 | 100 | 95 |
| 3 | 95 | 95 | 90 | 90 | 95 | 95 | 100 | 100 | 100 | 95 | 100 | 100 | 95 |
| 4 | 95 | 95 | 90 | 90 | 90 | 90 | 100 | 100 | — | — | 100 | 95 | 95 |
| 5 | 95 | 95 | 95 | 90 | 100 | 95 | 100 | 100 | — | — | 100 | 100 | 95 |

It has also been found that the abovementioned objectives could be attained by virtue of the combination of one or more compounds of formula (I) with at least one fungicide of the group (II), i.e. a fungicide chosen from the following subclasses:

1. Chlorinated or nitrated benzene derivatives such as quintozene or chlorothalonil,
2. Dicarboximide derivatives such as captan, folpet, captafol, iprodione and procymidone, 3. Derivatives containing one or more heterocyclic rings such as quinolines and morpholines.

4. Phosphorous acid derivatives such as metal phosphites.

5. Dithiocarbamic acid derivatives such as maneb or mancozeb.

6. Phenol derivatives such as dinocap.

7. Quinone derivatives such as dithianon.

8. Derivatives of carbamic acid and of benzimidazoles such as carbendazim, benomyl and methyl thiophanate.

9. Sulphur derivatives.

10. Amines and amides such as dichloran, carboxin, triforine, cymoxanil, metalaxyl and ofurace.

11. Diazines such as chinomethionat, fenarimol and anilazine.

12. Sulphamides such as dichlofluanide.

13. Guanidines such as doguadine.

14. Triazoles such as those described in British Patent No. 2,046,260, the content of which is incorporated by reference.

The active substances of group (II) are known active substances, most of them being described in detail in works such as "The Pesticide Manual" published by The British Crop Protection Council, the 7th edition of which dates from 1983.

The combinations according to the invention are in most cases of binary type (a single active substance of group II), but ternary (2 active substances of group II) or quaternary (3 active substances of group II) combinations are also sometimes employed.

Among the active substances of group II, further preference will be given to the following active substances: chlorothalonil, iprodione, fenpropimorph, tridemorph, dinocap, dithianon, maneb, mancozeb, Al-fosetyl, captane, carbendazim, captafol, sulphur and diniconazol.

The chemical names of the products listed above are indicated in the appended table with the use of AngloSaxon nomenclature, i.e. with the position of the substituents being indicated in front of the latter.

The weight ratio of the compound according to the invention to the active substances of group II described above is preferably between 0.0003 and 3,000 and advantageously between 0.001 and 1,000.

It is also possible to combine insecticides, repellents and germination regulators with the compounds or combinations described above.

| TABLE OF NOMENCLATURE | |
|---|---|
| Chlorothalonil | Tetrachloroisophthalonitrile |
| Iprodione | 3-(3,5-Dichlorophenyl)-N-isopropyl-2,4-dioxoimidazolidine-1-carboxamide |
| Fenpropimorph | (±)-Cis-4-[3-(4-tert-butylphenyl)-2-methylpropyl]-2,6-dimethylmorpholine |
| Tridemorph | 2,6-Dimethyl-4-tridecylmorpholine |
| Dinocap | 2-(1-Methylheptyl)-4,6-dinitrophenyl crotonate |
| Dithianon | 5,10-Dihydro-5,10-dioxonaphtho[2,3-b]-1,4-dithiaanthraquinone |
| Maneb | Manganese ethylenebis(dithiocarbamate) |
| Mancozeb | Complex of maneb with a zinc salt |
| Al-fosetyl | Aluminium tris-0-ethylphosphonate |
| Captane | N-(Trichloromethylthio)cyclohex-4-ene-1,2-dicarboximide |
| Carbendazim | Methyl benzimidazol-2-ylcarbamate |
| Captafol | N-(1,1,2,2-Tetrachloroethylthio)cyclohex-4-ene-1,2-dicarboximide |
| Diniconazol | 1-(2,4-Dichlorophenyl)-4,4-dimethyl-2-(1,2,4-triazol-1-yl)-1-penten-3-ol. This latter product is described in |

-continued

| TABLE OF NOMENCLATURE |
|---|
| Patent GB 2,046,260, already mentioned |

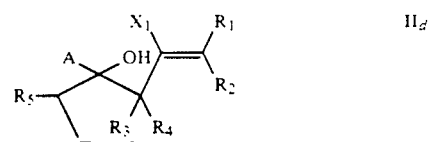

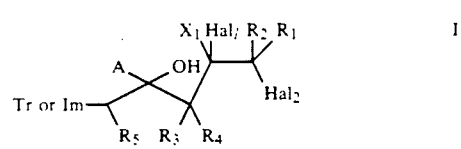

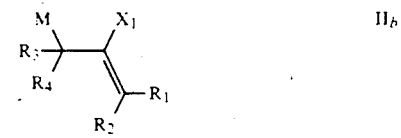

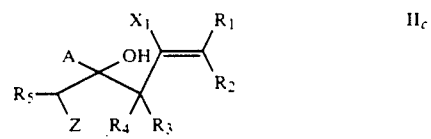

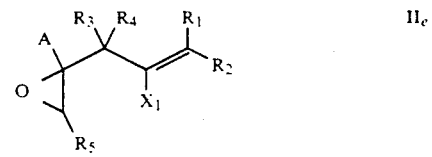

We claim:

1. A triazole compound of the formula

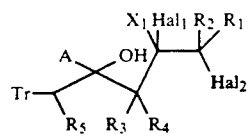

or agriculturally acceptable salts thereof wherein

A is $(Y)_n Ph—(CH_2)_m$ wherein Ph is a phenylene nucleus;

m is 0 or 1;

each Y is independently halogen, cyano, nitro, lower alkyl, lower alkoxy, phenyl, phenoxy, benzyl or benzyloxy, said alkyl, alkoxy, phenyl, phenoxy, benzyl or benzyloxy groups being unsubstituted or substituted with halogen;

n is 0–5;

Tr is 1, 2, 4-triazol-1-yl;

$R_1$, $R_2$, $R_3$, $R_4$ and $R_5$ may be the same or different and are hydrogen, lower alkyl, lower cycloalkyl, phenyl, benzyl, lower alkoxy, lower alkanoyl, or benzoyl, said alkyl, cycloalkyl, phenyl, benzyl, alkoxy, alkanoyl, or benzoyl groups are either independently unsubstituted or substituted with halogen or lower alkoxy;

X₁ is hydrogen, halogen, lower alkyl, lower cycloalkyl, phenyl, benzyl, said alkyl, cycloalkyl, phenyl or benzyl groups being unsubstituted or substituted with halogen or lower alkoxy; or X₁ is Q—R₆, in which Q is O or S and R₆ is hydrogen, lower alkyl, lower cycloalkyl, phenyl, benzyl, lower alkanoyl, thio lower alkanoyl, lower alkyloxythioyl, phenoxythioyl or benzyloxythioyl, said Q—R₆ may be unsubstituted or substituted with halogen or lower alkoxy; or X₁ is a group NR₈R₉ in which R₈ and R₉ are independently hydrogen, lower alkyl, lower cycloakyl, phenyl or benzyl, said alkyl, cycloakyl, phenyl or benzyl groups being unsubstituted or substituted with halogen or lower alkoxy; or Hal₁ and Hal₂, which may be the same or different, are halogen.

2. The compound according to claim 1 wherein m is 0.

3. The compound according to claim 1 wherein Q—R₆ is acetyl, thioacetyl, propionyl or thiopropionyl.

4. The compound according to claim 1 in which Hal₁ and Hal₂ may be the same or different and are bromine or chlorine.

5. The compound according to claim 1 wherein Hal₁ and Hal₂ are the same.

6. The compound according to claim 1 wherein Y is halogen and n is 1, 2 or 3.

7. The compound according to claim 6 wherein Y is chlorine.

8. The compound according to claim 6 wherein Y is a halogen atom in the ortho or para position on the phenylene and n is 1 or 2.

9. The compound according to claim 8 wherein R₁, R₂, R₃, R₄, R₅ and X₁ are each independently hydrogen or lower alkyl and Hal₁ and Hal₂ are each chlorine.

10. The compound according to claim 9 wherein R₁, R₂, R₃, R₄, R₅ and X₁ are hydrogen.

11. The compound according to claim 1 which is 1-[2-(2,4-dichlorophenyl)-2-hydroxy-4,5-dibromopentyl](1H)-1,2,4-triazole.

12. A method of combatting fungicidal disease in plants which comprises applying to plants infected with said disease an anti-fungicidal effective amount of the compound according to claim 1.

13. A fungicidal composition which contains as an active substance a fungicidally effective amount of a compound according to claim 1 and an agriculturally acceptable inert carrier therefor.

14. The composition according to claim 13 wherein the fungicidally effective amount ranges from 0.5 to 95% by weight.

15. The method according to claim 12 wherein the effective amount ranges from 0.005 to 5 kg/ha.

16. The method according to claim 15 wherein the effective amount ranges from 0.01 to 0.5 kg/ha.

17. The method according to any one of claims 15 and 24 wherein the fungal disease in piricularioses, mildews or rusts or crops.

* * * * *

UNITED STATES PATENT AND TRADEMARK OFFICE
CERTIFICATE OF CORRECTION

PATENT NO. : 5,124,344
DATED : June 23, 1992
INVENTOR(S) : Alfred Greiner, et al.

It is certified that error appears in the above-identified patent and that said Letters Patent is hereby corrected as shown below:

Column 8, line 11: "Example 5" should read as --Example F 5--

Column 16, line 30, Claim 17: "24" should read as --16--

Signed and Sealed this

Twelfth Day of October, 1993

Attest:

BRUCE LEHMAN

*Attesting Officer*     *Commissioner of Patents and Trademarks*